(12) United States Patent
Nguyen et al.

(10) Patent No.: US 11,739,359 B2
(45) Date of Patent: Aug. 29, 2023

(54) UNIVERSAL TEMPLATE STRANDS FOR ENZYMATIC POLYNUCLEOTIDE SYNTHESIS

(71) Applicant: MICROSOFT TECHNOLOGY LICENSING, LLC, Redmond, WA (US)

(72) Inventors: Bichlien Nguyen, Seattle, WA (US); Jake Smith, Seattle, WA (US); Robert Carlson, Seattle, WA (US); Karin Strauss, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 533 days.

(21) Appl. No.: 16/865,262

(22) Filed: May 1, 2020

(65) Prior Publication Data
US 2021/0340615 A1   Nov. 4, 2021

(51) Int. Cl.
*C12P 19/34* (2006.01)
*C12N 15/10* (2006.01)
(Continued)

(52) U.S. Cl.
CPC .............. *C12P 19/34* (2013.01); *C12N 15/10* (2013.01); *C12Q 1/68* (2013.01); *C12Q 1/6834* (2013.01);
(Continued)

(58) Field of Classification Search
None
See application file for complete search history.

(56) References Cited

U.S. PATENT DOCUMENTS 6,136,568 A * 10/2000 Hiatt ................... C12N 15/1027
536/23.1
2019/0144887 A1* 5/2019 George ................ C12N 15/905
435/6.15

FOREIGN PATENT DOCUMENTS

WO    2017007925 A1    1/2017
WO    2019224544 A1    11/2019

OTHER PUBLICATIONS

Watkins et al. Nearest-neighbor thermodynamics of deoxyinosine pairs in DNA duplexes. Nucleic Acids Research 33(19):6258-6267. (Year: 2005).*

(Continued)

*Primary Examiner* — Samuel C Woolwine
(74) *Attorney, Agent, or Firm* — Benjamin Keim; Newport IP, LLC

(57) ABSTRACT

A universal template strand built with universal base analogs is used as a template for polynucleotide synthesis. The universal template strand can hybridize to any sequence of nucleotides. A new polynucleotide is synthesized by using a polymerase to extend a primer hybridized to the universal template strand. Unlike primer extension in polymerase chain reactions, base pairing with nucleotides in the template strand does not specify the sequence of the new polynucleotide. Instead, the sequence of the new polynucleotide is specified by the order of addition of protected nucleotides. After addition of a single species of protected nucleotide, the blocking group is removed and another protected nucleotide is added. The order of nucleotide addition can be varied to create any sequence. After synthesis, the polynucleotide can be dehybridized from the universal template strand. The universal template strand may then be reused to synthesize a different polynucleotide.

20 Claims, 10 Drawing Sheets

(51) Int. Cl.
  *C12Q 1/68* (2018.01)
  *C12Q 1/6834* (2018.01)
(52) U.S. Cl.
  CPC . *C12Q 2521/101* (2013.01); *C12Q 2521/131* (2013.01); *C12Q 2525/101* (2013.01); *C12Q 2525/186* (2013.01); *C12Q 2533/101* (2013.01)

(56) References Cited

OTHER PUBLICATIONS

Egeland et al. Nucleic Acids Research 33(14):e125. (Year: 2005).*
"International Search Report & Written Opinion issued in PCT Application No. PCT/US21/023790", dated Aug. 23, 2021, 16 Pages.
Chen, et al., "The History and Advances of Reversible Terminators Used in New Generations of Sequencing Technology", In Journal Genomics, Proteomics & Bioinformatics, vol. 11, Issue 1, Feb. 2013, pp. 34-40.
Liang, et al., "Universal Base Analogues and Their Applications in DNA Sequencing Technology", In Journal of the Royal Society of Chemistry Advances, vol. 3, Issue 35, Jun. 6, 2013, pp. 14910-14928.
Loakes, David, "Survey and Summary: The Applications of Universal DNA Base Analogues", In Journal of Nucleic Acids Research, vol. 29, Issue 12, Jun. 15, 2001, pp. 2437-2447.
Pipkorn, et al., "Improved Synthesis Strategy for Peptide Nucleic Acids (PNA) appropriate for Cell-specific Fluorescence Imaging", In International Journal of Medical Sciences, vol. 9, Issue 1, 2012, pp. 1-10.
Li, et al., "Multistep DNA-Templated Synthesis Using a Universal Template", In Journal of the American Chemical Society, vol. 135, Issue 47, Nov. 18, 2013, pp. 17727-17730.
Organick, et al., "Random Access in Large-Scale DNA Data Storage", In Journal of the Nature Biotechnology, vol. 36, Issue 3, Mar. 1, 2018, pp. 242-248.
"Invitation to Pay Additional Fees Issued in PCT Application No. PCT/US21/023790", dated Jul. 2, 2021, 13 Pages.

* cited by examiner

UNIVERSAL BASE ANALOGUE STRUCTURES 300

HYDROGEN BONDING BASES 302

HYPOXANTHINE
(INOSINE)

7-DEAZAHYPOXANTHINE

2-AZAHYPOXANTHINE

2-HYDROXYPURINE

PURINE

4-AMINO-1H-PYRAZOLO
[3,4-D]PYRIMIDINE

PI-STACKING BASES 304

NITROIMIDAZOLE

INDOLE

BENZIMIDAZOLE

5-FLUOROINDOLE

5-NITROINDOLE

N-INDOL-5-YL-FORMAMIDE

ISOQUINOLINE

METHYLISOQUINOLINE

BACKBONE STRUCTURES 400

DEOXYRIBOSE PHOSPHATE
402

R = H, Ak

RIBOSE PHOSPHATE
404

PEPTIDE NUCLEIC ACID
406 n = 0, 1, 2

LOCKED NUCLEIC ACIDS
408

R = H, Ak, Ar

BRIDGED NUCLEIC ACIDS
410

UNIVERSAL TEMPLATE STRANDS FOR ENZYMATIC POLYNUCLEOTIDE SYNTHESIS

BACKGROUND

There are several techniques for artificially synthesizing polynucleotides. At present, the majority of artificially synthesized oligonucleotides are created by chemical synthesis using the phosphoramidite process. Polynucleotides are also be synthesized enzymatically with a template-independent deoxyribonucleic acid (DNA) polymerase such as terminal deoxynucleotidyl transferase (TdT).

Phosphoramidite synthesis is carried out by stepwise addition of nucleotide residues to the 5'-terminus of a growing polynucleotide until the desired sequence is assembled. Phosphoramidite synthesis involves a complex series of chemical reactions to join nucleoside phosphoramidites and creates organic waste that can be hazardous and expensive to process. Enzymes used for enzymatic synthesis, such as TdT, can repeatedly add any available nucleotide in an unregulated manner. Multiple techniques have been developed to regulate the activity of template-independent polymerases. However, it can still be difficult to add only a single nucleotide at a time. The techniques for constraining activity of template-independent polymerases each increase complexity of the process and have their own set of drawbacks.

Alternative ways of creating polynucleotides that avoid the limitations of current chemical and enzymatic synthesis techniques can have broad applications in many areas that use artificial polynucleotides. The following disclosure is made with respect to these and other considerations.

SUMMARY

This disclosure provides methods and devices for synthesizing polynucleotides by using a universal template strand that includes universal base analogs that pair with any of the natural nucleotide bases. Primer extension with polymerase is used to synthesize a polynucleotide with a de novo sequence that is "complementary" to the universal template strand. The universal template strand creates a double-stranded molecule with the growing polynucleotide. A double-stranded molecule is necessary for some polymerases, such as DNA-dependent DNA polymerases, to incorporate nucleotides on the end of a growing polynucleotide. In some implementations, the universal template strand may have a backbone structure that is different from conventional DNA or ribonucleic acid (RNA).

Because the universal template strand can hybridize to any sequence, the sequence of the polynucleotide hybridized to the universal template strand is specified not by base pairing with the template strand but by the order in which protected nucleotides are added. Protected nucleotides include blocking groups that limit addition to only one nucleotide at a time. After a protected nucleotide is incorporated into a growing polynucleotide by a polymerase, the blocking group is removed and the next protected nucleotide is added. Multiple cycles of protected nucleotide addition and deblocking are repeated until synthesis of the polynucleotide is complete. The polynucleotide may be dehybridized from the universal template strand and stored or processed. The universal template strand may then be reused to create a different polynucleotide.

Multiple polynucleotides with different sequences can be created in parallel by anchoring universal template strands to a solid substrate and selectively deblocking protected nucleotides at only specific locations on the surface of the solid substrate. Location-specific deblocking may be achieved by any number of techniques that cause cleavage of blocking groups at some but not all of the nucleotides attached to the solid substrate. Techniques for controlling the locations at which blocking groups are removed include using a microelectrode array to vary electrical current, a photomask to control exposure to light, and inkjet printing to deposit chemicals at precise locations. Different combinations of locations on the surface of the solid substrate may be deblocked at each cycle which changes where protected nucleotides are added. Performing multiple cycles of addition in which the location of nucleotide addition and the base of the nucleotide are varied each cycle creates a high degree of parallelism and enables synthesis of a batch of polynucleotides with different sequences.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
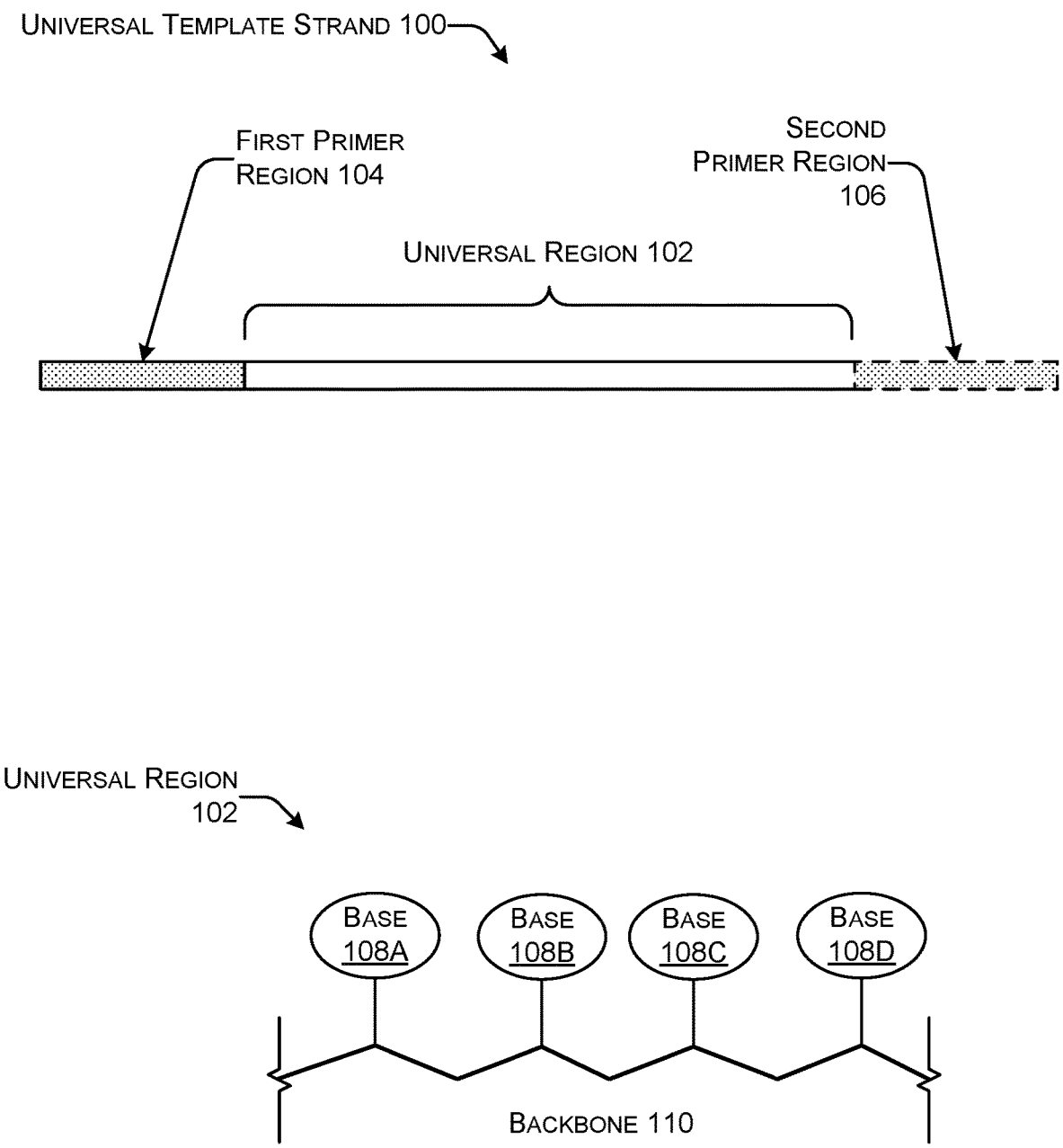
FIG. 1 shows a schematic diagram of a universal template strand.

This disclosure provides techniques and systems that use universal template strands to synthesize polynucleotides with specific, arbitrary sequences. These assembly techniques are alternatives to conventional phosphoramidite polynucleotides synthesis and enzymatic synthesis using TdT. The synthesis techniques presented in this disclosure may use the same enzymes as typical polymerase chain reaction (PCR). In PCR, a polymerase adds nucleotides that are complementary to a template strand. Complementary relationships are created by Watson-Crick base pairing in which adenine (A) pairs with thymine (T) and cytosine (C) pairs with guanine (G). With PCR the complement of an existing sequence is created. PCR is not able to generate new and arbitrary polynucleotide sequences but can increase the number of copies of existing sequences.

However, the techniques presented herein create de novo sequences through use of a "template" strand that contains universal base analogs. Universal base analogs can pair to any of the four natural nucleotide bases. Thus, the universal template strand does not provide a template that specifies a nucleotide sequence through complementary base pairing relationships. Rather, the universal template strand provides a second polynucleotide strand that enables the use of DNA-dependent DNA polymerases that require a double-stranded structure to incorporate nucleotides.

Polymerases include DNA-dependent DNA polymerases and template-independent polymerases. All polymerase are enzymes that synthesize DNA from deoxyribonucleotides or RNA from ribonucleotides. Polymerase can add free nucleotides only to the 3' end of a newly forming strand. This results in elongation of the newly forming strand in a 5'-3' direction. No known polymerase can begin a new chain (de novo). Polymerases can only add a nucleotide onto a pre-existing 3'-OH group, and therefore use a primer to which the first nucleotide is added.

Polynucleotides, also referred to as oligonucleotides, include both DNA, RNA, and hybrids containing mixtures of DNA and RNA. DNA includes nucleotides with one of the four natural bases cytosine (C), guanine (G), adenine (A), or thymine (T) as well as unnatural bases, noncanonical bases, and modified bases. RNA includes nucleotides with one of the four natural bases cytosine, guanine, adenine, or uracil (U) as well as unnatural bases, noncanonical bases, and modified bases. Nucleotides include both deoxyribonucleotides and ribonucleotides covalently linked to one or more phosphate groups. The term "polynucleotide sequence" refers to the alphabetical representation of a polynucleotide molecule. The alphabetical representation may be input and stored the memory of a computing device.

PCR is a molecular biology technique known to those of skill in the art. PCR is a reaction for making multiple copies or replicates of a target nucleic acid flanked by primer binding sites. The reaction comprising one or more repetitions of the following steps: (i) denaturing the target nucleic acid, (ii) annealing primers to the primer binding sites, and (iii) extending the primers by a template-dependent polymerase in the presence of nucleoside triphosphates. Usually, the reaction is cycled through different temperatures optimized for each step in a thermocycler.

Particular temperatures, durations at each step, and rates of change between steps depend on many factors well-known to those of ordinary skill in the art, e.g., exemplified by the references: McPherson et al., editors, *PCR: A Practical Approach and PCR 2: A Practical Approach* (IRL Press, Oxford, 1991 and 1995, respectively). Illustrative methods for detecting a PCR product using an oligonucleotide probe capable of hybridizing with the target sequence or amplicon are described in Mullis, U.S. Pat. Nos. 4,683,195 and 4,683,202; EP No. 237,362. Techniques for performing conventional PCR may be adapted by the skilled artisan and used to synthesize polynucleotides with universal template strands.

Primers used with DNA-dependent DNA polymerases hybridize to a portion of the template strand that has a complementary nucleotide sequence. By "hybridize" or "complement" or "substantially complement" it is meant that a polynucleotide comprises a sequence of nucleotides that enables it to non-covalently bind, to another polynucleotide in a sequence-specific, antiparallel, manner (i.e., a polynucleotide specifically binds to a complementary polynucleotide) under the appropriate conditions of temperature and solution ionic strength.

Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein; and Sambrook, J. and Russell, W., Molecular Cloning: *A Laboratory Manual, Third Edition*, Cold Spring Harbor Laboratory Press, Cold Spring Harbor (2001). The conditions of temperature and ionic strength determine the "stringency" of the hybridization. For example, hybridize or hybridization may refer to the capacity for hybridization between two single-stranded polynucleotides or polynucleotide segments at 21° C. in 1× TAE buffer containing 40 mM TRIS base, 20 mM acetic acid, 1 mM ethylenediaminetetraacetic acid (EDTA), and 12.5 mM $MgCl_2$.

Detail of procedures and techniques not explicitly described or other processes disclosed of this application are understood to be performed using conventional molecular biology techniques and knowledge readily available to one of ordinary skill in the art. Specific procedures and techniques may be found in reference manuals such as, for example, Michael R. Green & Joseph Sambrook, *Molecular Cloning: A Laboratory Manual*, Cold Spring Harbor Laboratory Press, $4^{th}$ ed. (2012).

FIG. 1 shows a schematic diagram of a universal template strand 100. The universal template strand is a single-stranded molecule that includes a universal region 102 which comprises universal base analogs. A universal base analog is a nucleotide base that forms "base pairs" with each of the natural DNA/RNA bases with little discrimination between them. Thus, any other base may be paired with a universal base analog in a double-stranded polynucleotide. The universal region 102 may also include standard nucleotides that follow conventional base pairing rules as well as bases that are not "universal" analogs but that pair with two or three the natural bases.

The universal template strand may also include a first primer region 104 and a second primer region 106. The first primer region 104 may hybridize with a first primer or a forward primer. The second primer region 106 may hybridize with a second primer or a reverse primer. The first primer region 104 and the second primer region 106 may include entirely or predominantly natural bases. The first primer region 104 and the second primer region 106 may have different lengths and in some implementations may each be independently between 10-30 nucleotides, 15-25 nucleotides, or 18-22 nucleotides long. The universal template strand 100 may also include other regions not shown. Other regions may be positioned adjacent to either of the first primer region 104 or the second primer region 106.

The first primer region 104 may have a nucleotide sequence that hybridizes strongly to the first primer creating a stable double-stranded structure. The strength of the hybridization of a primer can be represented by the primer melting temperature ($T_m$) which is defined as the temperature at which one half of a polynucleotide duplex will dissociate to become single stranded. Primer melting temperature indicates duplex stability. The GC content of a primer gives a fair indication of the primer $T_m$. Techniques and software for determining primer $T_m$ are known to those of ordinary skill in the art. See Kamel Abd-Elsalam, *Bioinformatic tools and guideline for PCR primer design*, Vol. 2 (5) African Journal of Biotechnology, 91-95 (2003) for a discussion of primer design tools. The $T_m$ of the first primer region 104 may be greater than 58° C., greater than 60° C., or greater than 62° C. The $T_m$ of the first primer region 104 may be between 52-68° C., between 55-65° C., or between 60-65° C. A strong hybridization between a primer and the first primer region 104 may support double-strand stability by compensating for the weak association of universal base analogs with natural nucleobases.

The optional second primer region 106, if present, may have characteristics that are the same or similar to the first primer region 104. The second primer region 106 may also differ from the first primer region 104 by having a lower $T_m$ than the first primer region.

The universal region 102 contains a series of bases 108 attached to a backbone. The universal region 102 may be any length that can be created by current or future synthesis techniques. In some implementations, a length of the universal region 102 may be about 100-200 bases long. For simplicity, FIG. 1 illustrates only four bases 108A, 108B, 108C, and 108D (collectively base(s) 108). The bases 108 may be the same throughout the entire length of the universal region 102. Thus, there may be only one type of base 108 in a universal region 102. Alternatively, two or more different types of bases 108 may be present in the universal region 102. For example, there may be multiple different types of universal base analogs present in the universal region 102 either as an ordered or random mixture of universal base types.

In one implementation, natural bases may be interspersed with universal base analogs at regular intervals. For example, natural bases may be present at regular intervals in alternation with universal base analogs in a 1:1 ratio. Thus, in this example, bases 108A and 108C are universal base analogs and bases 108B and 108D are natural bases. Other ratios of natural bases to universal base analogs are also possible such as 1:2, 1:3, 1:4, 1:5, 1:6, 1:7, 1:8, 1:9, 1:10, etc. By way of explanation, a ratio of 1:10 would have one natural base followed by 9 universal base analogs. Without being bound by theory, it is believed that the inclusion of natural bases in the universal region 102 may help double-stranded stability through hydrogen bonding.

The presence of known natural bases at known positions in the universal region 102 may be used as reference or validation signals when processing sequence reads of polynucleotides synthesized by this technique. Each natural base in the universal region 102 should pair with its complementary natural base in the final polynucleotide that is synthesized. This pattern should be present in sequence reads generated by sequencing the polynucleotide. Thus, if there is a known pattern in the polynucleotides, for example an adenine (A) base every tenth position, then sequence reads can be examined to determine if that pattern is present. If it is not, then the read may be discarded or interpreted differently. The pattern of known bases in the final sequence read may also be used to align multiple polynucleotide sequences to, for example, generate a consensus sequence.

The backbone 110 may be a standard deoxyribose phosphate backbone (found in DNA) or a ribose phosphate backbone (found in RNA). The backbone 110 may also include non-natural structures such as ribose phosphate with a 2'-deoxy substitution, peptide nucleic acids, locked nucleic acids, and bridged nucleic acids. Any combination of backbone structures may be combined in the backbone 110. For example, the backbone 110 may include deoxyribose phosphate regions and peptide nucleic acid regions. For example, the backbone 110 may include locked nucleic acids and bridged nucleic acids.

Locked nucleic acids and bridged nucleic acids form more ridged and stable structures than natural polynucleotide backbones. Peptide nucleic acids form more stable structures when bound to polynucleotides than natural polynucleotide backbones. Without being bound by theory, it is believed that the use of an artificial backbone may increase the stability of the universal template strand 100. It is also known that some artificial backbone structures are resistant to enzymatic digestion. The increased stability and resistance to digestion may be beneficial if the universal template strand 100 is reused multiple times for synthesis of multiple different polynucleotides. Use of an artificial backbone that is resistant to enzymatic degradation may allow for use of an enzymatic clean-up step to remove unwanted oligonucleotides such as primers and free nucleotides without damaging the universal template strand 100.

The universal template strand 100 may be created by any suitable technique for polymerizing nucleotides with natural bases and with universal base analogs. In some implementations, the universal template strand 100 is created by solid-phase synthesis. The specific technique will vary with the type of backbone 110. DNA with a deoxyribose phosphate backbone or strands with other ribose-based backbones may be synthesized by the standard phosphoramidite process. Techniques for phosphoramidite synthesis, including solid-phase synthesis, are well known to those of skill in the art. Strands with peptide nucleic acid backbones may be created by a modification of Fmoc-based peptide synthesis. One example technique for creating polynucleotides with peptide nucleic acid backbones is described in, Rudiger Pipkorn, et al., *Improved Synthesis Strategy for Peptide Nucleic Acids (PNA) appropriate for Cell-specific Fluorescence Imaging*, Int J Med Sci 9(1):1-10 (2012).

FIGS. 2A, 2B, 2C, and 2D (collectively FIG. 2), show an illustrative time series 200 of schematic diagrams illustrating the synthesis of multiple different polynucleotides with universal template strands 100 attached to a solid substrate 202. The solid substrate 202 is illustrated with only four universal template strands 100 but it is to be understood that the solid substrate 202 may be coated with hundreds, thousands, or millions of universal template strands 100.

The solid substrate 202 is coated with universal template strand 100 attached to the surface of the solid substrate 202 through functionalization or by a linker. Many linkers and other techniques for attaching polynucleotides to the surface of a substrate are known to those of ordinary skill in the art. Examples include silane functionalization which covers a surface with organofunctional alkoxysilane molecules or agarose functionalization which covers a surface with polysaccharide matrix. Non-covalent attachment such as streptavidin-biotin interactions may also be used to attach the universal template strands 100 to the solid substrate 202.

In an alternate implementation (not shown), the first primer 206 may be attached to the surface of the solid substrate 202. The first primer 206 may be the distal end of a longer oligonucleotide that is anchored to the solid substrate 202. A linker molecule may attach the first primer 206 to the solid substrate 202. The universal template strand 100 is then hybridized to the first primer 206 but is not itself directly connected to the substrate 202.

In an implementation, the solid substrate 202 may be a microelectrode array. A microelectrode array is an array that contains many small, spatially addressable electrodes. In some implementations, the solid substrate 202 may be an integrated circuit (IC) constructed using complementary metal-oxide-semiconductor (CMOS) technology. The CMOS may include metal-oxide-semiconductor field-effect transistors (MOSFETs) made through a triple-well process or by a silicon-on-insulator (SOI) process.

The microelectrode array may contain a large number of microelectrodes that make it possible to create many different oligonucleotides (e.g., 10,000, 60,000, 90,000, or more) on the surface of a single array. This high level of multiplexing is made possible in part by the microelectrode density which may be approximately 1000 microelectrodes/$cm^2$, 10,000 microelectrodes/$cm^2$, or a different density. Examples of suitable microelectrode arrays are provided in Bo Bi et al., *Building Addressable Libraries: The Use of "Safety-Catch" Linkers on Microelectrode Arrays*, 132 J. Am. Chem. Soc. 17, 405 (2010) and in U.S. patent application Ser. No. 16/435,363 filed on Jun. 7, 2019, with the title "Reversing Bias in Polymer Synthesis Electrode Array."

Individual or groups of universal template strands 100 may be attached in proximity to electrodes of the microelectrode array. Proximity as used in this context means close enough to undergo a physical or chemical change in response to a change of the electrode potential of an electrode. The change in electrode potential may trigger cleavage of a linker or release of a blocking group.

Timepoint 204 shows first primers 206 hybridized to the universal template strands 100 at or near the point of connection to the solid substrate 202. The first primers 206 hybridize to the first primer region 104 shown in FIG. 1. Hybridization may be performed under stringent conditions to prevent the first primers 206 from hybridizing to the universal region 102 of the universal template strands 100.

The first primers 206 may include blocking groups 208. Blocking groups 208 are represented as octagons in this schematic illustration. However, in some implementations the first primers 206 may not include blocking groups 208. A blocking group 208 prevents extension of the first primer 206. After removal of the blocking group 208, the first primer 206 can be extended by incorporation of nucleotides by a polymerase. The blocking groups 208 may be located on the 3'-end of the primers 206. Removal of a 3' blocking group 208 replaces the blocking group 208 with a 3' hydroxyl group. Suitable 3' blocking groups and methods for removing the 3' blocking groups include, but are not limited to, the 3' blocking groups and methods described in U.S. Pat. No. 7,541,444. All of the first primers 206 may be identical in both nucleotide sequence and type of blocking group 208.

The blocking groups 208 may be thermolabile blocking groups that are removed by heat in the absence of enzymes, chemical reagents, and the like. Examples of thermolabile blocking groups include those described in U.S. Publication Nos. 2010/0003724 and 2007/0281308.

An linkers used to attach dyes in sequencing-by-synthesis applications may be used to attach blocking groups 208. In some implementations, the dye or fluorophore used for sequencing-by-synthesis may be the blocking group 208. Examples of linkers used in sequencing-by-synthesis applications are provided in Fei Chen, et. al., *The History and Advances of Reversible Terminators Used in New Generations of Sequencing Technology*, 11 Genomics Proteomics Bioinformatics 34-40 (2013).

The blocking groups 208 may be removed by redox reactions. Examples of redox-cleavable 3' blocking groups include hydroxylamine and azidomethyl groups. The allyl blocking group is cleavable by $Pd_0$. Redox reactions may be initiated by activation of individual electrodes of a microelectrode array.

The blocking groups 208 may be photolabile. Photolabile blocking groups are removed by exposure to a specific wavelength of light. There are a large number of known types of photo-cleavable linkers that can attach blocking groups 208. Common classes of photolabile linkers include nitrobenzyl-based linkers, benzyl nitrile-based linkers, benzyl-based linkers, and carbonyl-based linkers. Amine-to-thiol cross-linkers are also photolabile and may be lengthened by attachment to a polyethylene glycol (PEG) chain. Amine-to-thiol bonds may be cleaved by ultraviolet (UV) light with a wavelength of about 365-405 nm. One example of a photocleavable blocking group is the "virtual terminator" described in Bowers J, et al. *Virtual terminator nucleotides for next-generation DNA sequencing*. Nat Methods (2009) 6:593-5.

Timepoint 210 shows selective deblocking of some but not all of the first primers 206. Selective deblocking is achieved by spatial control of conditions on the surface of the solid substrate 202. At selected, specific locations the conditions are changed so that any blocking groups 208 at those locations are released. The change may be a change in electrical current due to the activation of an electrode in a microelectrode array. The change may be a change in temperature caused by the activation of resistors. The change may be exposure to light controlled by optoelectronics or by applying light through a lithographic photomask. The change may be addition of a chemical agent such as an acid or base controlled by chemical inkjet printing. Examples of techniques for changing local conditions on the surface of a solid substrate are discussed in U.S. patent application Ser. No. 16/230,787 entitled "Selectively Controllable Cleavable Linkers" filed on Dec. 21, 2018.

Timepoint 212 shows the first primers 206 without blocking groups 208 extended by addition of first protected nucleotides 214 and polymerase. Polymerase adds the first protected nucleotides 214 onto the ends of unblocked first primers 206. The blocking group 208 used on the first protected nucleotides 214 may be the same as the blocking used on the first primer 206. In this example, two of the four first primers 206 are extended by addition of an adenine (A) nucleotide. The other first primers 206 are not extended resulting in the creation of different sequences. If the first primers 206 do not include blocking groups, then the first cycle of nucleotide addition will add a first protected nucleotide 214 to all of the first primers 206.

In implementations, the polymerase may be a DNA-dependent DNA polymerase or a template-independent polymerase. DNA-dependent DNA polymerases, also called template-dependent polymerases, require a template strand with an attached primer (e.g., first primer 206) to initiate synthesis. There are many commercially available DNA-dependent DNA polymerases provided for use in PCR that are suitable for the techniques of this disclosure. Examples of DNA-dependent DNA polymerases include *E. coli* DNA polymerase I and its Klenow fragment, T4 DNA polymerase, native and modified T7 DNA polymerase, phi29 DNA polymerase, Bst DNA polymerase, and Taq DNA polymerase, Deep Vent® DNA Polymerase (available from New England Biolabs, Inc.), Q5® high-fidelity DNA polymerase (available from New England Biolabs, Inc.), and KAPA HiFi DNA polymerase (available from Roche Diagnostics). Characteristics and reaction conditions of the DNA-dependent DNA polymerases are known to those of skill in the art and are available from the supplier and/or presented in reference material such as Kucera, R. B. and Nichols, N. M., *DNA-Dependent DNA Polymerases*, 84 Current Protocols in Molecular Biology, 3.5.1-3.5.19 (2008).

Template independent polymerases are DNA or RNA polymerases that perform de novo oligonucleotide synthesis without use of a template strand. Currently known template-independent polymerases include TdT, poly(A) polymerase, and tRNA nucleotidyltransferase. TdT adds nucleotides indiscriminately to the 3' hydroxyl group at the 3' end of single-stranded DNA. TdT performs unregulated synthesis adding any available deoxynucleotide triphosphate (dNTP). TdT uses an existing single-stranded polynucleotide referred to as an "initiator" as the starting point for synthesis. Although TdT performs unregulated synthesis and does not require a template strand if provided with protected nucleotides TdT can be constrained to add only a single nucleotide. After addition, the added nucleotide will align with the universal template strand (even though that strand was not required by TdT) because of hydrogen bonding and/or base stacking interactions.

TdT evolved to rapidly catalyze the linkage of naturally occurring deoxynucleotide triphosphates (dNTPs). TdT adds nucleotides indiscriminately to the 3' hydroxyl group at the 3' end of single-stranded DNA. TdT performs unregulated synthesis adding any available dNTP. TdT uses an existing single-stranded polynucleotide referred to as an "initiator" as the starting point for synthesis. Initiators as short as three nucleotides have been successfully used with TdT for enzymatic synthesis of DNA. Suitable initiator length ranges from three nucleotides to about 30 nucleotides or longer. The first primer 206 may be the initiator for TdT. During the polymerization, the template independent polymerase holds a single-stranded DNA strand (which initially is only the initiator) and adds dNTPs in a 5'-3' direction. TdT activity is maximized at approximately 37° C. and performs enzymatic reactions in an aqueous environment.

Figure 2A:
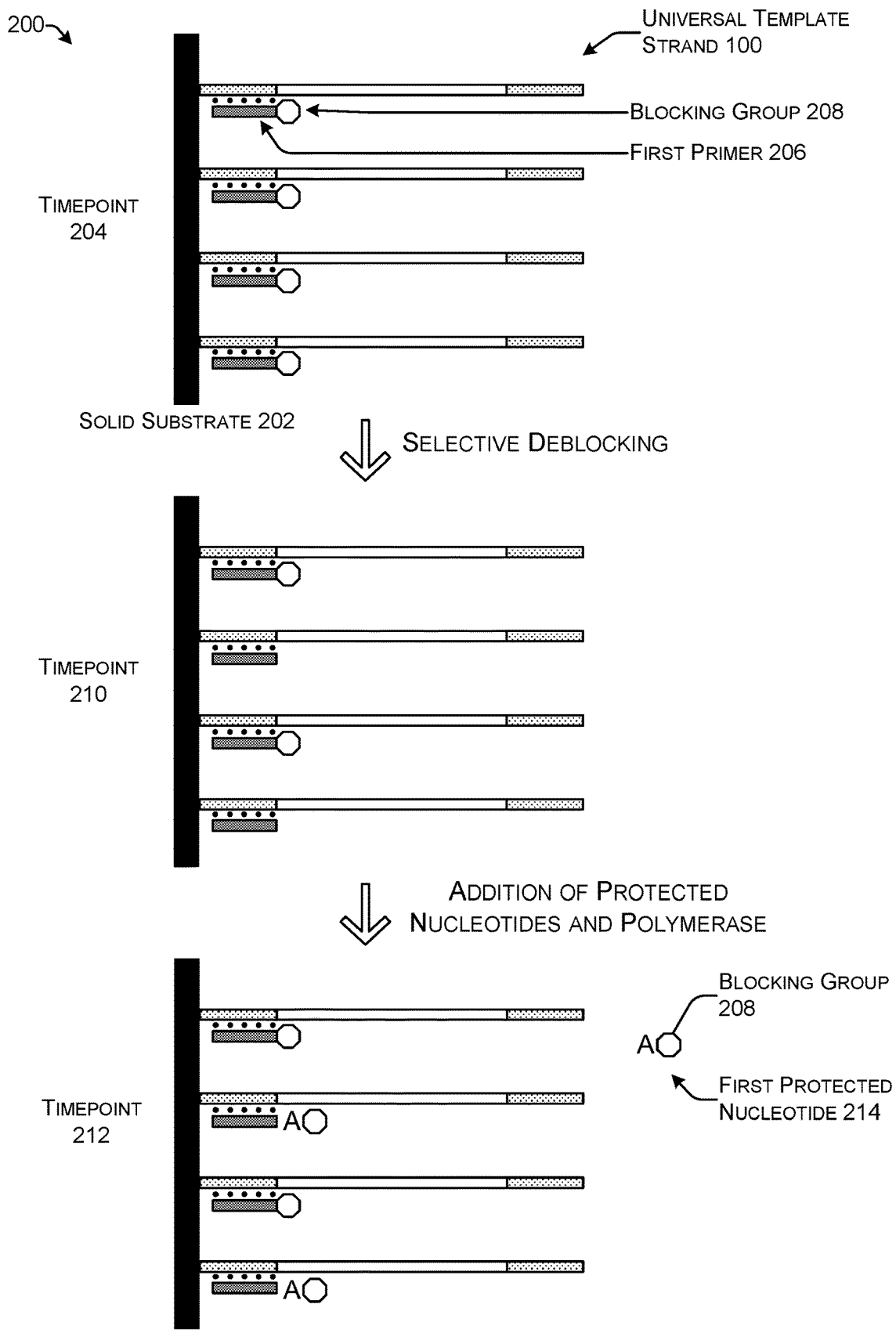
FIGS. 2A-D show a series of schematic diagrams illustrating the synthesis of multiple different polynucleotides with universal template strands attached to a solid substrate.
Figure 2B:
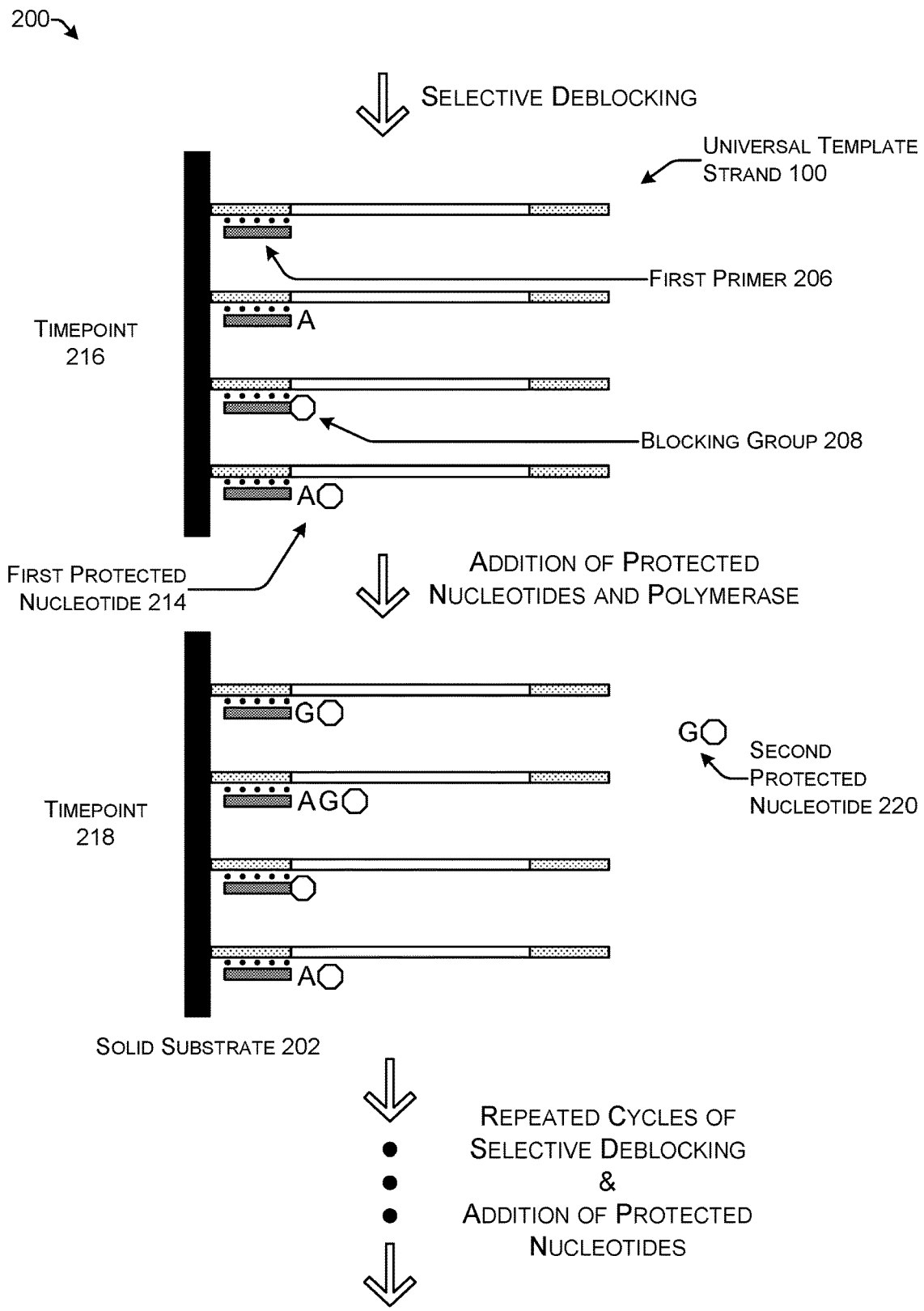

FIG. 2B shows a second cycle of selective deblocking that removes blocking groups from specific locations on the surface of the solid substrate 202 at timepoint 216. The second cycle of selective deblocking may remove some blocking groups from first primers 206 and some blocking groups 208 from first protected nucleotides 214 added during a previous cycle. Thus, each cycle of selective deblocking may remove blocking groups 208 at different locations on the surface of the solid substrate 202. However, there may also be two or more sequential cycles in which selective deblocking occurs at the same locations. There may also be cycles in which deblocking occurs at all of the universal template strands 100 bound to the solid substrate 202 (e.g., all electrodes of a microelectrode array are activated or a deblocking reagent is flooded across the whole surface of the solid substrate 202).

Selective deblocking is again followed by the addition of second protected nucleotides 220 and polymerase. This is shown in timepoint 218 where the second protected nucleotide 220 is illustrated as having a guanine (G) base. Of course, any sequence of nucleotide bases may be added. The second protected nucleotide 220 is added at all locations that are not protected by a blocking group 208. In this example, that includes a first primer 206 and a first protected nucleotide 214 added during a previous cycle.

Repeated cycles of selective deblocking and addition of protected nucleotides in the presence of a polymerase extend the first primers 206 to create growing polynucleotides that form double-stranded structures with the universal template strands 100. The protected nucleotides that are available in solution to be added to the ends of growing polynucleotides may be changed during each cycle of synthesis. The species of protected nucleotide added during a cycle controls "what" is added (e.g., A, G, C, or T) each cycle. The locations of selective deblocking controls "where" addition occurs. By varying what is added and where additions occur, it is possible to synthesize a population of polynucleotides at on the surface of the solid substrate each with a different sequence. This is a highly parallel technique for de novo synthesis of polynucleotides that can use DNA-dependent DNA polymerases in a novel way.

Figure 2C:
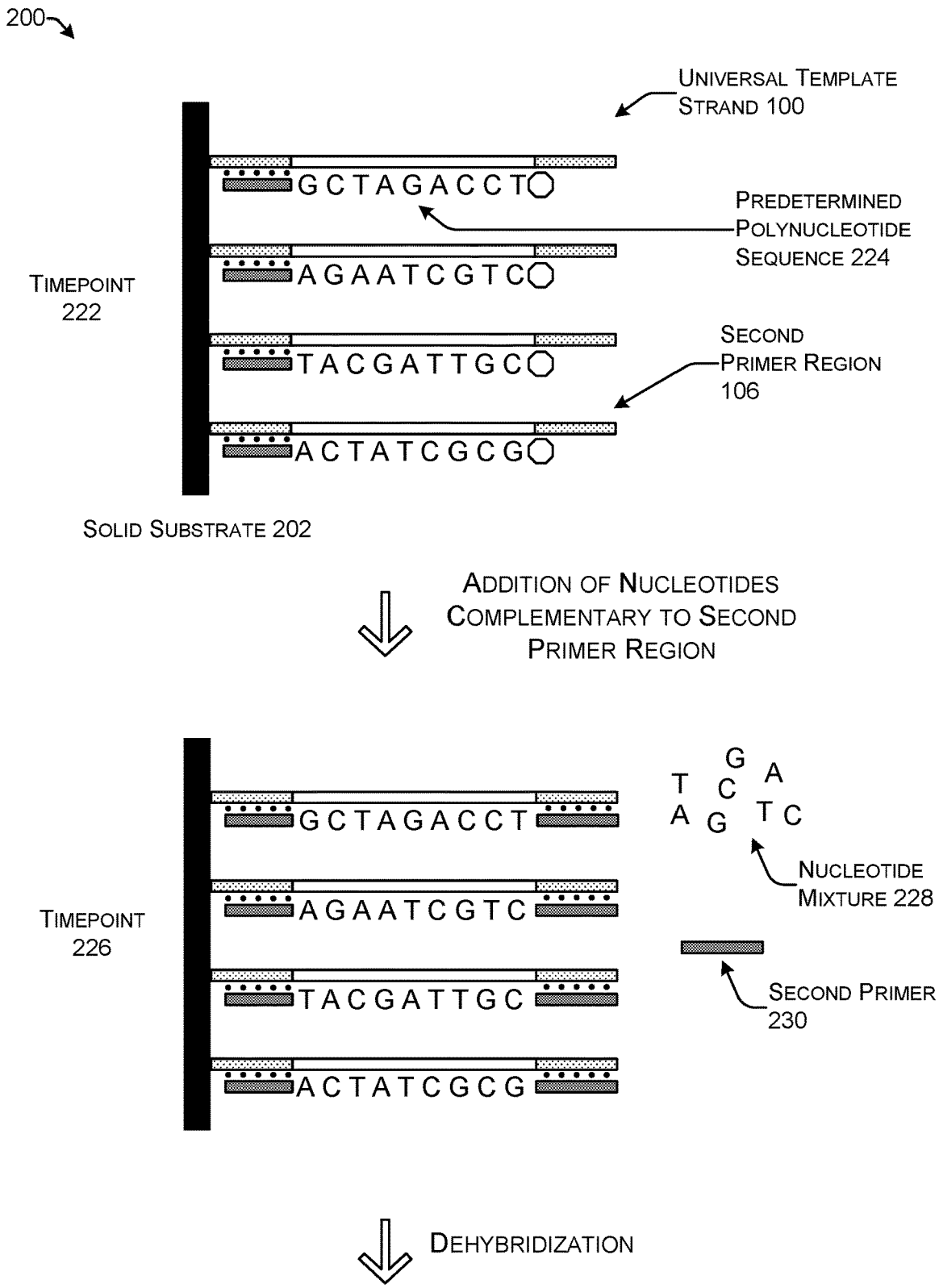

FIG. 2C shows the results of multiple cycles of deblocking and the addition of protected nucleotides at timepoint 222. Each of the universal template strands 100 is now paired with a polynucleotide that each has a predetermined polynucleotide sequence 224. The predetermined polynucleotide sequences 224 may be determined in advance of synthesis as with any other technique for artificial synthesis of polynucleotides. For example, the predetermined polynucleotide sequences 224 may be manually specified by a human user or generated by a computer system. In FIG. 2 the predetermined polynucleotide sequences 224 are shown as having only nine nucleotides, but in practice are generally longer and may include about 100-200 nucleotides.

In some implementations, the predetermined polynucleotide sequences 224 may encode digital data. The specific polynucleotide sequence of nucleotide bases (e.g., GCTA-GACCT) may encode a bit sequence (e.g., 011010). Proof of concept systems and techniques for storing data in polynucleotides have been previously demonstrated. See Lee Organick et al., *Random Access in Large-Scale DNA Data Storage*, 36:3 Nat. Biotech. 243 (2018) and Christopher N. Takahashi et al., *Demonstration of End-to-End Automation of DNA Data Storage*, 9 Sci. Rep. 4998 (2019).

The universal template strands 100 may include a second primer region 106 as shown in FIG. 1. Timepoint 226 illustrates techniques for creating a nucleotide sequence complementary to the second primer region 106. The second primer region 106 is created from standard nucleobases and can provide a template for synthesis of a complementary strand using conventional PCR primer extension techniques. Thus, in one implementation, a nucleotide mixture 228 (e.g., a mixture of dNTPs such as commercially available dNTPs mixes for use in PCR) may be added in the presence of polymerase. The polymerase extends the predetermined polynucleotide sequence 224 by addition of nucleotide triphosphates that are complementary to the nucleotides in the second primer region 106. The nucleotides in the nucleotide mixture 228 may be unprotected nucleotides without blocking groups 208.

In an implementation, a second primer 230 complementary to the second primer region 106 may be added. The second primer 230 hybridizes to the second primer regions 106 of the universal template strands 100. A backbone nick between the end of the predetermined polynucleotide sequence 224 may be closed by ligase. Techniques for performing ligation and closing of nicks in polynucleotides are well-known to those of ordinary skill in the art. The second primers 230 may be synthesized by any current or future technique for synthesizing oligonucleotides such as phosphoramidite synthesis.

Once the polynucleotides hybridized to the universal template strands 100 are completely synthesized, the doubled-stranded structures may be dehybridized. Unlike PCR, dehybridization does not occur after each set of annealing and extension. Rather, there is a dehybridization step only after the full-length polynucleotides are synthesized. The synthesized polynucleotides and the universal template strands 100 may be separated from each other by any known or later developed technique for dehybridizing double-stranded polynucleotides. Known variables that affect dehybridization include temperature, pH, helicase enzymes, binding proteins, hydrogen bonding disruptors, and ionic strength of a buffer/electrolyte solution. Any of these, or other, variables may be modified to dehybridize the two strands.

Figure 2D:
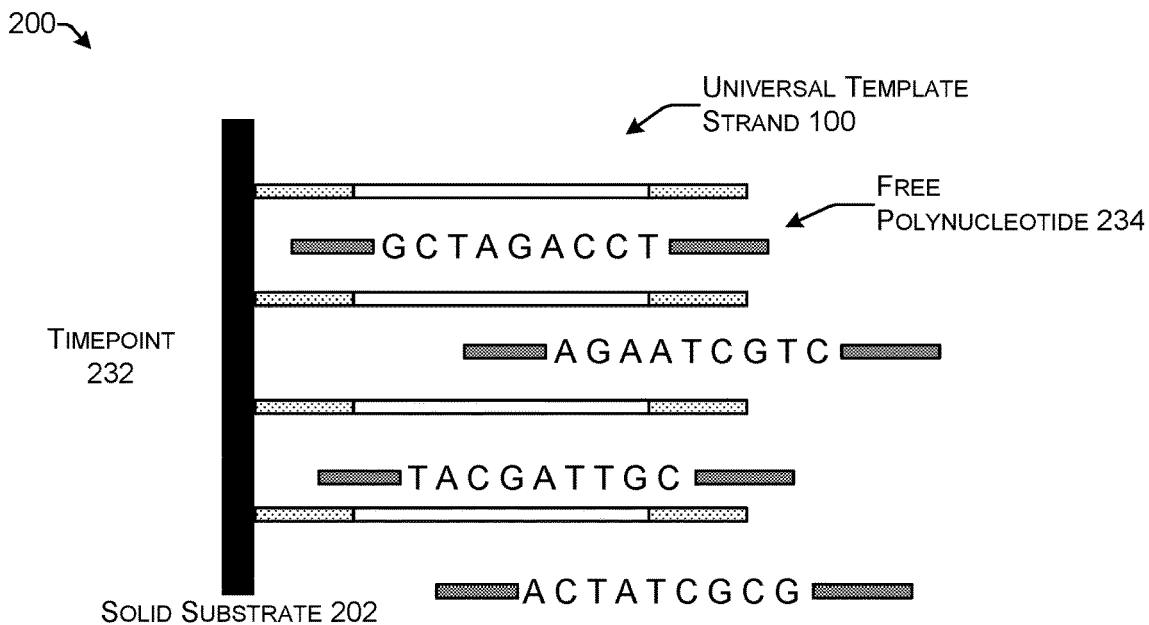
Figure 2D:
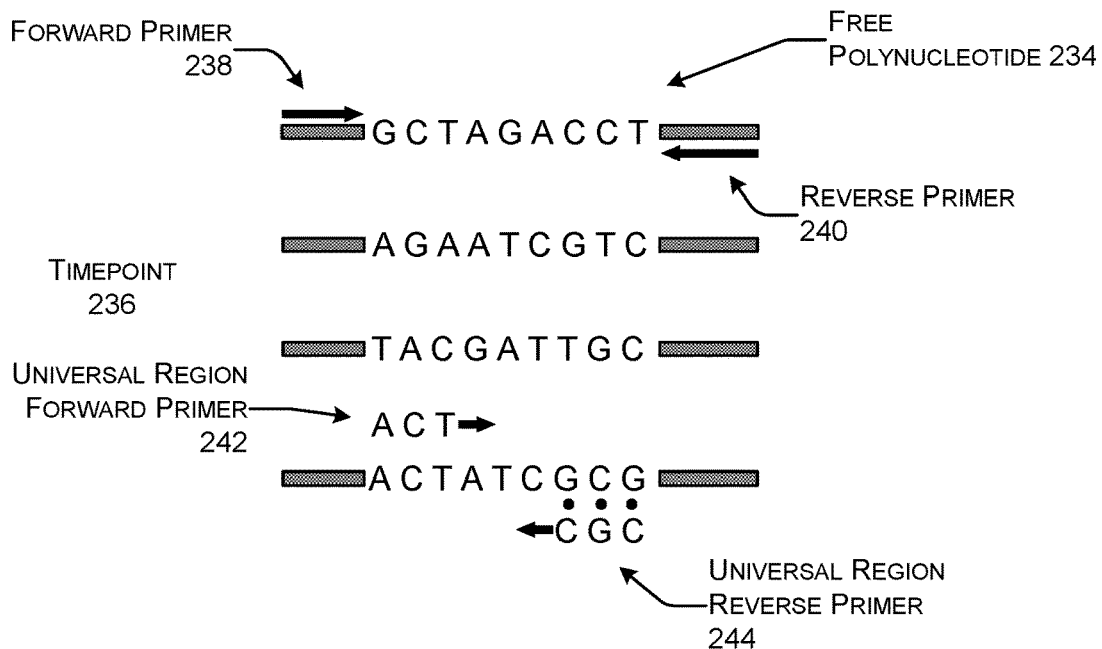

FIG. 2D shows the result of dehybridization at timepoint 232. Free polynucleotides 234 are present in the solution that covers the surface of the solid substrate 202. Once the free polynucleotides 234 are in solution, they may be stored or processed like any other polynucleotide. The solution that covers the surface of the solid substrate 202 and contains the free polynucleotides 234 may be collected and stored. Before storage or other processing, the free polynucleotides 234 may be cleaned. Many techniques for polynucleotide clean-up are known to those of skill in the art such as phenol-chloroform extraction, ethanol precipitation, silica column-based kits, anion exchange, and magnetic beads. The solid substrate 202 with the attached universal template strands 100 may be washed and reused to create a new batch of polynucleotides with different sequences.

In an implementation in which the first primer 206 instead of the universal template strand 100 is anchored to the solid substrate 202, dehybridization will release the universal template strands 100 which may be collected and reused. The polynucleotides that were synthesized remain bound to the surface of the solid substrate 202. If a linker, nucleotide sequence, or other structure that binds the first primer 206 to the solid substrate 202 is cleaved, this will release the free nucleotides 234. The solid substrate 202 may then be re-coated with oligonucleotide strands that have the same or different sequences as the first primer 206.

One type of processing for the free polynucleotides 234 is PCR amplification. In some implementations, each of the free polynucleotides 234 will have the same sequences preceding and following the predetermined polynucleotide sequences 224—specifically the first primer region 104 and the second primer region 106. Thus in such implementations, PCR using a forward primer 238 and a reverse primer 240 can amplify all of the free polynucleotides 234. Due to the complementary relationship between the universal template strand 100 and the free polynucleotides 234, the forward primer 238 may have the same sequence as all or part of the first primer region 104 and reverse primer 240 may have the same sequences as all or part of the second primer region 106.

PCR amplification may also be performed without using both, or either, of the first primer region 104 or the second primer region 106. Primers may be designed that hybridize to portions of the free polynucleotides 234 synthesized from a universal region 102 of a universal template strand 100. These are referred to here as a universal region forward primer 242 and a universal region reverse primer 244. The sequence of the free polynucleotides 234 are known allowing for the design of complementary primers. The universal region forward and reverse primers 242, 244 may both independently be short oligonucleotides (e.g., about 10-30 nucleotides) that are complementary to specific ones of the free polynucleotides 234. Because the universal region forward and reverse primers 242, 244 do not necessarily hybridize to all of the free polynucleotides 234, they can be used for selective amplification. Thus, further processing of the free polynucleotides 234 may include using primers and PCR to amplify some but not all of the polynucleotides synthesized in the same batch.

In implementations where the universal template strands 100 lack the second primer region 106, PCR may be performed using the forward primer 238 and one or more universal region reverse primers 244 or random primers in place of the reverse primer 240. Amplification products made with any set of primers be stored, sequenced, or otherwise processed.

Figure 3:
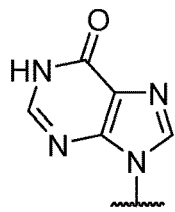
FIG. 3 illustrates examples of universal base analog structures that may be used in a universal template strand.
Figure 3:
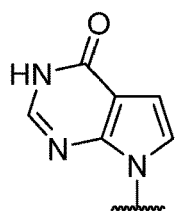
Figure 3:
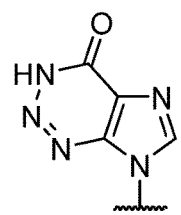
Figure 3:
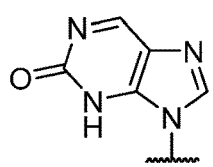
Figure 3:
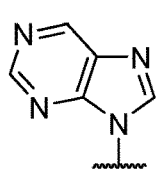
Figure 3:
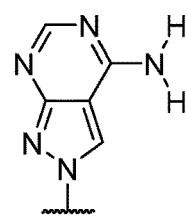
Figure 3:
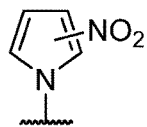
Figure 3:
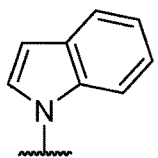
Figure 3:
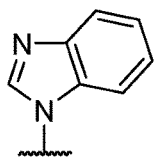
Figure 3:
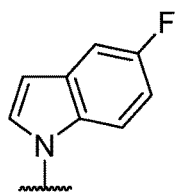
Figure 3:
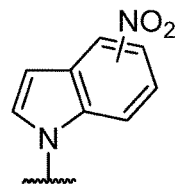
Figure 3:
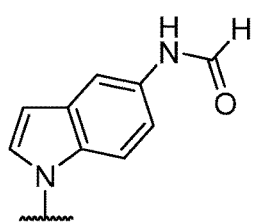
Figure 3:
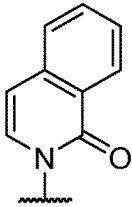
Figure 3:
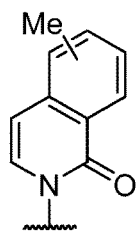

FIG. 3 illustrates examples of universal base analog structures 300. A universal base analog is a nucleotide base that can form "base pairs" with each of the natural DNA/RNA bases with little discrimination between them. Universal base analogs may be divided into hydrogen bonding bases 302 and pi-stacking bases 304. Hydrogen bonding bases 302 form hydrogen bonds with any of the natural nucleobases. The hydrogen bonds formed by hydrogen bonding bases 302 are weaker than the hydrogen bonds between natural nucleobases. Pi-stacking bases are non-hydrogen bonding, hydrophobic, aromatic bases that stabilize duplex polynucleotides by stacking interactions.

Examples of hydrogen bonding bases 302 include, but are not limited to, hypoxanthine (inosine), 7-deazahypoxanthine, 2-azahypoxanthine, 2-hydroxypurine, purine, and 4-Amino-1H-pyrazolo [3,4-d]pyrimidine. In an implementation, universal base analogs included in the bases 108 in the universal region 102 of the universal template strand 100 shown in FIG. 1 are hydrogen bonding bases 302. In an implementation, all universal base analogs included in the bases 108 in the universal region 102 are inosine or derivatives thereof. Examples of pi-stacking bases include, but are not limited to, nitroimidazole, indole, benzimidazole, 5-fluoroindole, 5-nitroindole, N-indol-5-yl-formamide, isoquinoline, and methylisoquinoline. Examples of universal bases are discussed in Berger et al., *Universal Bases for Hybridization, Replication and Chain Termination*, Nucleic Acids Research 2000, August 1, 28(15) pp. 2911-2914; David Loakes, *The Applications of Universal DNA Base Analogs*, 29(12) Nucleic Acids Research 2437 (2001); and Feng Liang et al., *Universal base analogs and their applications in DNA sequencing technology*, 3 RSC Advances 14910-14928 (2013).

Figure 4:
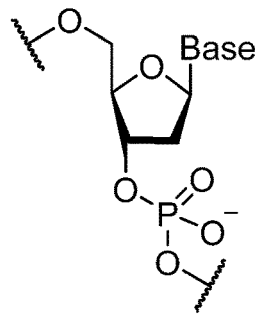
FIG. 4 illustrates examples of backbone structures that may be used in a universal template strand.
Figure 4:
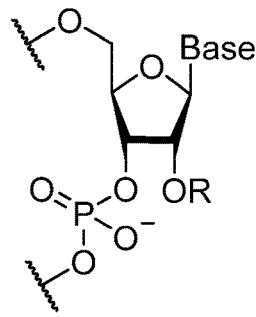
Figure 4:
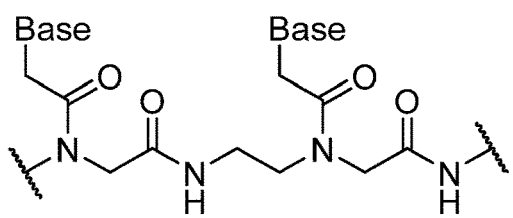
Figure 4:
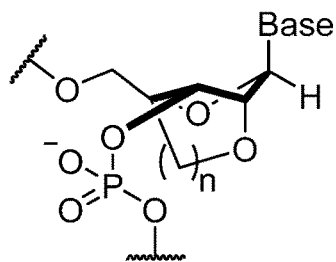
Figure 4:
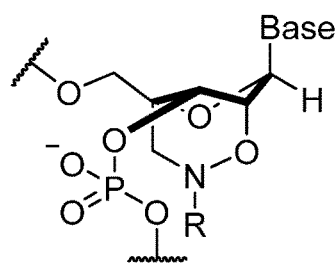

FIG. 4 shows examples of backbone structures 400 that may be present in the backbone 110 of the universal template strand 100 shown in FIG. 1. Any of the backbone structures 400 may be used separately or in combination to form the backbone 110. The backbone structures include deoxyribose phosphate 402 and ribose phosphate 404. Ribose phosphate 404 includes natural ribose phosphate with a 2' hydroxyl group and modified ribose phosphate. Modified ribose phosphate has a 2'-deoxy substitution that replaces the 2' hydroxyl group with a —O-akyl group such as 2'-O-methyl or 2'-O-propyl.

Peptide nucleic acid 406 is a nucleobase oligomer in which the natural backbone is replaced by a backbone composed of N-(2-aminoethyl)glycine units. In other words, peptide nucleic acid can be regarded as DNA with a neutral peptide backbone instead of a negatively charged sugar-phosphate backbone. Peptide nucleic acids 406 are chemically stable and not easily recognized by either nucleases or proteases, making them resistant to degradation by enzymes.

Locked nucleic acids 408 are modified RNA nucleotides in which the ribose moiety is modified with an extra bridge connecting the 2' oxygen and 4' carbon. The bridge "locks" the ribose in the 3'-endo (North) conformation. The locked ribose conformation enhances base stacking and backbone pre-organization. This significantly increases the stability and raises the melting temperature of polynucleotides with backbones of locked nucleic acids 408. Locked nucleic acid 408 monomers can be incorporated into polynucleotides using standard phosphoramidite chemistry.

Bridged nucleic acids 410 are modified RNA nucleotides that contain a bridge at the 2', 4'-position of the ribose to create a five-membered, six-membered, or even a seven-membered bridged structure with a "fixed" C3'-endo sugar puckering. Bridged nucleic acids 410 are structurally rigid nucleotides with increased binding affinities and stability as compared to natural backbones as well as resistance to exo- and endonucleases. Bridged nucleic acid 410 monomers can be incorporated into polynucleotides using standard phosphoramidite chemistry.

Figure 5:
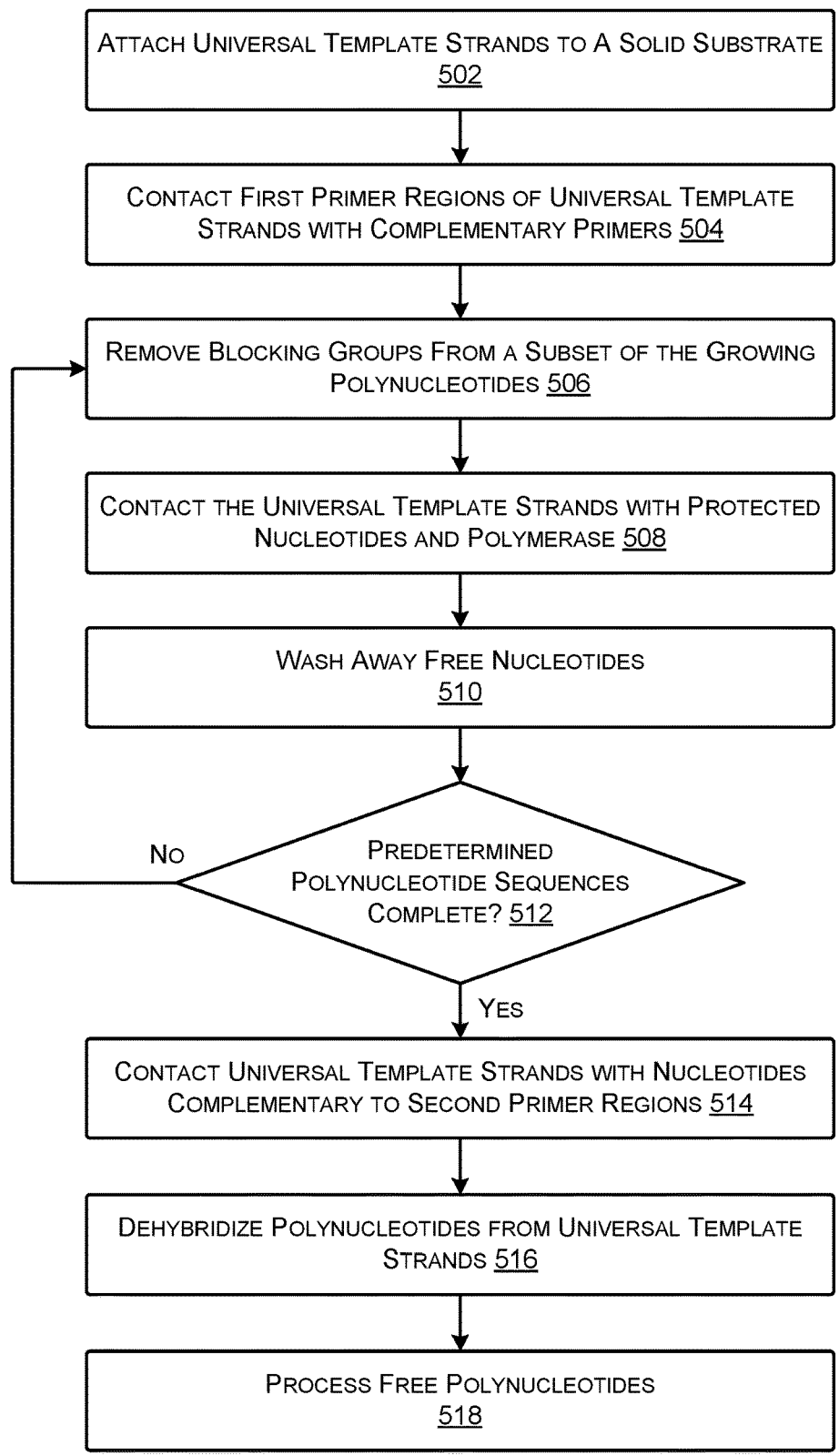
FIG. 5 is a flow diagram showing an illustrative process for synthesizing polynucleotides with universal template strands.

FIG. 5 shows a process 500 for synthesizing polynucleotides with universal template strands. Process 500 may be implemented, for example, using any of the techniques, universal base analogs, backbone structures, or systems shown in the other figures of this disclosure.

At operation 502, universal template strands are attached to a solid substrate. The universal template strands may be attached by any conventional technique for attaching polynucleotides sequences to solid substrates. For example, the surface of the solid substrate may be coated with linker molecules that in turn attach to an end of the universal template strands. As a further example, the surface of the solid substrate array may be functionalized through silanization or by coating with agarose. This creates a solid substrate that is coated with a plurality of anchor sequences. In some implementations, the solid substrate may be a microelectrode array. The solid substrate that is coated with universal template strands may be reused multiple times.

At operation 504, first primer regions of the universal template strand are contacted with complementary primers (e.g., forward primers). The universal template strands may be contacted with the complementary primers by covering the surface of the solid substrate with a solution that contains an excess of the complementary primers. The first primer regions of the universal template strands may be the portions of the universal template strands that are attached to or closest to the surface of the solid substrate. The complementary primers may be short oligonucleotides that are about 15-25 nucleotides long. In some implementations, the complementary primers may include blocking groups. The blocking groups may be 3' blocking groups. In an implementation, the complementary primers may hybridize strongly to the first primer regions with a $T_m$ that is greater than 60° C.

After contacting with the primers, there may be an initialization step that includes heating to about 95° C. for about 10 seconds followed by a drop in temperature that is below the $T_m$ of the complementary primers. For example, if the $T_m$ of a complementary primer is 60° C. then the temperature may be decreased to about 58° C.

The complementary primers and the first primer regions may both be created with natural nucleobases. Thus, the complementary primers hybridize to the first primer regions through standard Watson-Crick base pairing. This may be followed by a washing step to remove any complementary primers that have not hybridized to a universal template strand.

At operation 506, blocking groups are removed from a subset of the growing polynucleotides hybridized to the universal template strands. The growing polynucleotides begin as the complementary primers and are extended by single nucleotide addition (and possibly addition of other segments such as a second primer site) until they become a full-length polynucleotide or a fully synthesized polynucleotide. The blocking groups may be thermolabile, acid-labile, redox-labile, or photolabile. Redox reactions that remove blocking groups or cleave linkers may do so through direct or indirect reactions. Direct reactions result in the cleavage or removal of a group due to the presence of electrons created by activation of an electrode. Indirect reactions are caused by an intermediate species which is created or itself activated by electrons generated at an electrode. For example, activation of an electrode may cause the generation of an acid or base that in turn causes cleavage of an acid-labile or base-labile linkage.

The subset of the growing strands corresponds to locations on the surface of the solid substrate where local conditions have been changed resulting in the release of blocking groups only at those locations. For example, local conditions may be changed by activating selected electrodes in a microelectrode array.

Initially, if the complementary primers include blocking groups all of the blocking groups will be on the complementary primers. However, protected nucleotides will be added to some of the growing polynucleotide strands each cycle. By the fifth cycle (i.e., after adding each of the four standard nucleotides) all blocking groups will be attached to protected nucleotides added during a previous cycle.

At operation 508, the universal template strands are contacted with protected nucleotides and polymerase. The polymerase may be a template-dependent polymerase or a template-independent polymerase. The protected nucleotides added during any cycle all have the same base. Thus, by providing only a single species of nucleotide (e.g., only adenine (A)) the polymerase is forced to add that species of nucleotide at all unblocked locations. Because the nucleotides are protected by blocking groups only a single nucleotide is added each cycle.

The blocking groups may be any type of known or later developed nucleotide blocking group. In an implementation, the blocking groups may be 3' blocking groups. One example of a blocking group is the 3'-O-azidomethyl reversible terminator used in sequencing-by-synthesis applications. See Chen supra for a discussion of this and other suitable nucleotide blocking groups.

This is an example of an extension step. The extension step is performed at a temperature suitable for activity of the polymerase which may be room temperature or a higher temperature (e.g., 72° C.) for about 1-5 seconds.

At operation 510, any protected nucleotides that remain free in solution may be washed away. This washing step can also remove the polymerase. Washing prevents protected nucleotides that have not been incorporated into a growing polynucleotide from being added during a subsequent cycle. This and other washing steps in process 500 may be performed with any suitable wash solution including, but not limited to, water and aqueous buffer solutions. Wash solutions compatible with polynucleotides and with polymerases are known to those of skill in the art.

At operation 512, it is determined if synthesis of the predetermined polynucleotide sequences is complete. Predetermined polynucleotide sequences are the arbitrary nucleotide sequences intended to be synthesized by process 500. It may not be possible to inspect the synthesized polynucleotides directly to determine if synthesis is complete, so the completion of synthesis may be inferred from aspects of the synthetic process that can be directly observed.

In an implementation, the predetermined polynucleotide sequences may be considered complete based on the number of cycles of nucleotide addition. For example, if a predetermined polynucleotide sequence (such as the predetermined polynucleotide sequence 224 shown in FIG. 2C) is 120 nucleotides long, synthesis may be considered complete after 120 cycles of nucleotide addition. In an implementation, the predetermined polynucleotide sequences may be considered complete based on the order of nucleotide addition. Each cycle of synthesis adds a protected nucleotide and the order of the bases in the predetermined polynucleotide sequences is known. Thus, after all the necessary nucleotides have been added in the correct order, synthesis may be considered complete. The number of cycles of nucleotide addition and order of nucleotide addition may both be evaluated to determine if synthesis is complete. When determining if synthesis of a group of different predetermined polynucleotide sequences is complete, the number of cycles of nucleotide addition and/or the order of nucleotide additions may be determined based on the number of cycles/nucleotide additions needed to synthesize the entire group of polynucleotides.

If the predetermined polynucleotide sequences have not yet been completely synthesized, then process 500 follows the "no" path and returns to operation 506. Repeated cycles of removal of blocking groups (operation 506), contacting with protected nucleotides (operation 508), and washing (operation 510) extend the complementary primers one nucleotide at a time to build full-length polynucleotides with the predetermined sequences. These repeated cycles are performed without dehybridization steps unlike PCR. The locations of deblocking and the species of protected nucleotide added can be (but are not necessarily) varied each cycle creating a population of polynucleotides with different sequences hybridized to the universal template strands attached to the solid substrate.

If the predetermined polynucleotide sequences are determined to have been completely synthesized, then process 500 follows the "yes" path and proceeds to operation 514. At operation 514, the universal template strands are contacted with nucleotides complementary to second primer regions. The second primer regions are optional regions of the universal template strands that include natural nucleobases. In an implementation, the second primer regions may be about 15-25 nucleotides long. Operation 514 may be omitted if the universal template strands do not include second primer regions.

In an implementation, the second primer regions may be contacted with a second primers that have natural nucleobases complementary to the nucleobases in the second primer regions. The second primers are then joined to the end of the polynucleotide by ligase to create a single polynucleotide strand that includes the first primer, a middle section that has the predetermined nucleotide sequence created by addition of single nucleotides, and the second primer. In an implementation, the second primer region may be contacted with a mixture of different species of nucleotides (e.g., all the natural nucleotides but mixtures of three or two different types of nucleotides are also possible) and polymerase. The nucleotides in the mixture do not include blocking groups and are added to the growing polynucleotide by polymerase in a sequence complementary to the second primer region.

At operation 516, the synthesized polynucleotides are dehybridized from the universal template strands. This releases the synthesized polynucleotides into the solution covering the surface of the solid substrate. One dehybridized, the synthesized polynucleotides may be referred to as free polynucleotides. Techniques for dehybridizing double-stranded polynucleotides are known to those of skill in the art and any suitable technique may be used.

At operation 518, the free nucleotides may be processed further. One type of processing that may be performed on the free polynucleotides is PCR amplification. The free polynucleotides may also be sequenced or stored.

Figure 6:
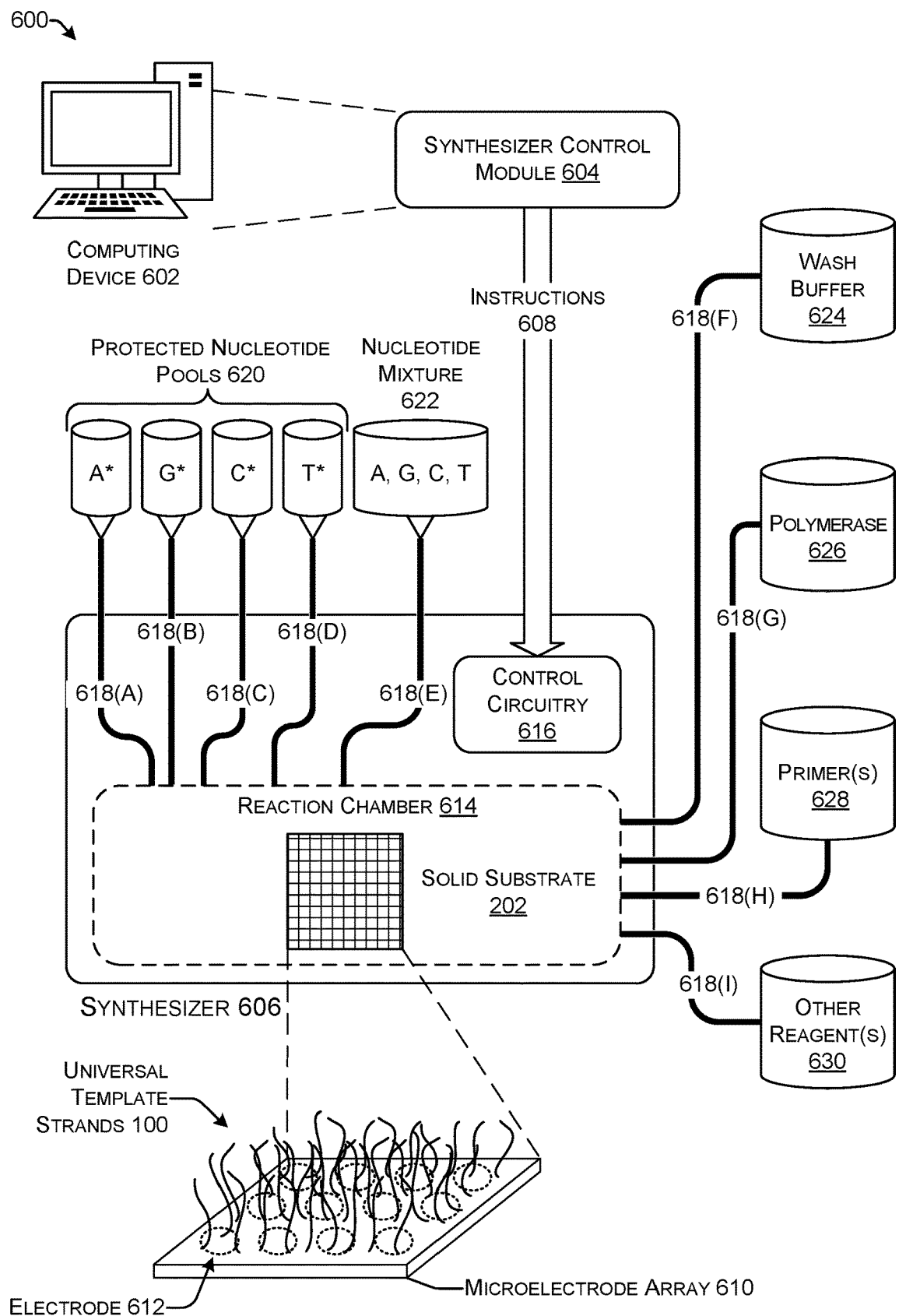
FIG. 6 is an illustrative system for synthesizing polynucleotides with universal template strands.

FIG. 6 shows an illustrative system 600 that may include a computing device 602 with a synthesizer control module 604 that is communicatively connected to a synthesizer 606. The synthesizer control module 604 may provide instructions 608 that control the operation of the synthesizer 606. The instructions may cause the synthesizer 606 to create polynucleotides with specific, predetermined sequences. The computing device 602 may be implemented as any type of conventional computing device such as a desktop computer, a laptop computer, a server, a hand-held device, or the like. In an implementation, the computing device 602 may be a part of the synthesizer 606 rather than a separate device.

The synthesizer 606 is a device that selectively assembles polynucleotides by hybridization to universal template strands 100 attached to a solid substrate 202. In one implementation the solid substrate 202 is a microelectrode array 610. Activation of an electrode 612 on the microelectrode array 610 releases blocking groups on nucleotides attached to the electrode 612. The solid substrate 202 may be located within a reaction chamber 614 or container capable of maintaining an aqueous or predominantly aqueous environment in contact with the surface of the solid substrate 202. The synthesizer 606 may also include a heater to control the temperature of aqueous solution in the reaction chamber 614. The heater may raise the temperature in the reaction chamber 614 to dehybridize polynucleotides from universal template strands 100.

As described above, the microelectrode array 610 includes a plurality of electrodes 612 that can be independently activated to vary the charge across the surface of the microelectrode array 610. In one example implementation, the microelectrode array 610 is functionalized by spin coating with a 3 wt % solution of agarose in 1× TBE buffer for 30 s at 1500 rpm. After coating, the microelectrode array 610 is baked at 50° C. for 1 h. This creates a surface with functional groups that can bind to the universal template strands 100. The universal template strands 100 may be synthesized directly onto the agarose coating using standard phosphoramidite reagents and methods. After preparation by this or another technique, the microelectrode array 610 may be placed in the synthesizer 606.

Control circuitry 616 may control the operation of the synthesizer 606. The control circuitry 616 may be implemented as any type of circuitry suitable for controlling hardware devices such as a printed circuit board, microcontroller, a programmable logic controller (PLC), or the like. The control circuitry 616 receives the instructions 608 provided by the synthesizer control module 604. The instructions 608 may indicate predetermined sequences of polynucleotides that are to be synthesized at individual electrodes 612 on the microelectrode array 610. The control circuitry 616 may be able to independently control the voltage at each of the electrodes 612 in the microelectrode array 610. The control circuitry 616 may also be able to activate fluid delivery pathways 618 that control the movement of fluids throughout the synthesizer 606 including in the reaction chamber 614. The fluid delivery pathways 618 may be implemented by tubes and pumps, microfluidics, laboratory robotics, or other techniques known to those of ordinary skill in the art.

Microfluidic technology facilitates the automation of chemical and biological protocols. These devices manipulate small quantities of liquid at smaller scales and with higher precision than humans. Digital microfluidic (DMF) technology is one type of flexible microfluidic technology. DMF devices manipulate individual droplets of liquids on a grid of electrodes, taking advantage of a phenomenon called electrowetting on dielectric. Activating electrodes in certain patterns can move, mix, or split droplets anywhere on the chip. Microfluidics also includes full-stack microfluidics which are programmable systems that allow unrestricted combination of computation and fluidics. Examples of microfluidic technology may be found in Willsey et al., *Puddle: A dynamic, error-correcting, full-stack microfluidics platform*, Aplos'19, April 13-17, 183 (2019).

In an implementation, the synthesizer 606 may include protected nucleotide pools 620. The protected nucleotide pools 620 may include a separate pool for each species of protected nucleotide (i.e., A, G, C, and T). Individual species of protected nucleotides are available to be separately transferred by a fluid delivery pathway 618(A), 618(B), 618(C), or 618(D) to the reaction chamber 614. The protected nucleotides may be stored in the pools 620 in an aqueous solution that uses a standard buffer for storing nucleotides.

There may also be a nucleotide mixture 622 that contains a mixture of nucleotides having two, three, or all four natural bases. The nucleotide mixture 622 may be a dNTP mixture. Nucleotides in the nucleotide mixture 622 do not include blocking groups. The nucleotide mixture 622 may be moved into the reaction chamber 614 through fluid delivery pathway 618(E).

One or more of a wash buffer 624, polymerase 626, primer(s) 628, and other reagent(s) 630 may also be available in pools connected to the reaction chamber 614 by respective fluid delivery pathways 618(F), 618(G), 618(H), and 618(I). The wash buffer 624 may be water or any wash buffer suitable for washing or manipulating polynucleotides such as TE, TAE, and TBE. The primer(s) 628 include one or more types of previously synthesized primers which may be any of the first primer 206, the second primer 230, the forward primer 238, or the reverse primer 240. Each type of primer may be stored in a separate pool and be connected to the reaction chamber 614 by a separate fluid delivery pathway. The other reagent(s) 630 may include DNA ligase or RNA ligase in appropriate buffer concentration for use in closing polynucleotide backbone nicks such as nicks resulting from addition of a second primer 230 as shown in FIG. 2C.

Illustrative Computer Architecture

Figure 7:
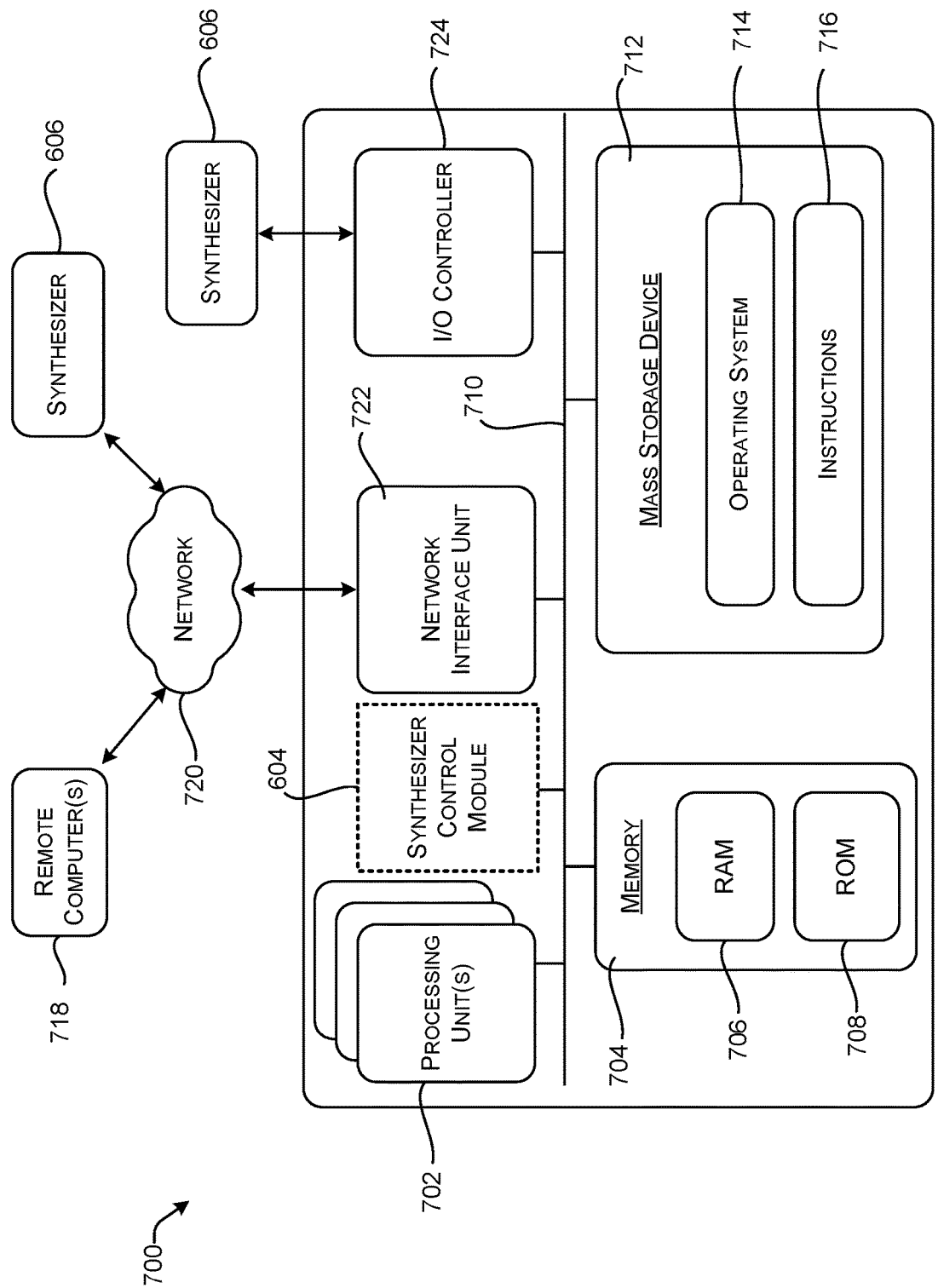
FIG. 7 is an illustrative computer architecture for implementing techniques of this disclosure.

FIG. 7 is a computer architecture diagram showing an illustrative computer hardware and software architecture for a computing device such as the computing device 602 introduced FIG. 6. In particular, the computer 700 illustrated in FIG. 7 can be utilized to implement the synthesizer control module 604.

The computer 700 includes one or more processing units 702, a system memory 704, including a random-access memory 706 ("RAM") and a read-only memory ("ROM") 708, and a system bus 710 that couples the memory 704 to the processing unit(s) 702. A basic input/output system ("BIOS" or "firmware") containing the basic routines that help to transfer information between elements within the computer 700, such as during startup, can be stored in the ROM 708. The computer 700 further includes a mass storage device 712 for storing an operating system 714 and other instructions 716 that represent application programs and/or other types of programs such as, for example, instructions to implement the synthesizer control module 604. The mass storage device 712 can also be configured to store files, documents, and data.

The mass storage device 712 may be connected to the processing unit(s) 702 through a mass storage controller (not shown) connected to the bus 710. The mass storage device 712 and its associated computer-readable media provide non-volatile storage for the computer 700. Although the description of computer-readable media contained herein refers to a mass storage device, such as a hard disk, CD-ROM drive, DVD-ROM drive, or USB storage key, it should be appreciated by those skilled in the art that computer-readable media can be any available computer-readable storage media or communication media that can be accessed by the computer 700.

Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner to encode information in the signal. By way of example, and not limitation, communication media includes wired media such as a wired network or direct-wired connection, and wireless media such as acoustic, radio frequency, infrared, and other wireless media. Combinations of any of the above should also be included within the scope of computer-readable media.

By way of example, and not limitation, computer-readable storage media can include volatile and non-volatile, removable and non-removable media implemented in any method or technology for storage of information such as computer-readable instructions, data structures, program modules or other data. For example, computer-readable storage media includes, but is not limited to, RAM 706, ROM 708, EPROM, EEPROM, flash memory or other solid-state memory technology, CD-ROM, digital versatile disks ("DVD"), HD-DVD, BLU-RAY, 4K Ultra BLU-RAY, or other optical storage, magnetic cassettes, magnetic tape, magnetic disk storage or other magnetic storage devices, or any other medium that can be used to store the desired information and which can be accessed by the computer 700. For purposes of the claims, the phrase "computer-readable storage medium," and variations thereof, does not include waves or signals per se or communication media.

According to various configurations, the computer 700 can operate in a networked environment using logical connections to the remote computer(s) 718 through a network 720. The computer 700 can connect to the network 720 through a network interface unit 722 connected to the bus 710. It should be appreciated that the network interface unit 722 can also be utilized to connect to other types of networks and remote computer systems. The computer 700 can also include an input/output controller 724 for receiving and processing input from several other devices, including a keyboard, mouse, touch input, an electronic stylus (not shown), or equipment such as a synthesizer 606 for synthesizing oligonucleotides. Similarly, the input/output controller 724 can provide output to a display screen or other type of output device (not shown).

It should be appreciated that the software components described herein, when loaded into the processing unit(s) 702 and executed, can transform the processing unit(s) 702 and the overall computer 700 from a general-purpose computing device into a special-purpose computing device customized to facilitate the functionality presented herein. The processing unit(s) 702 can be constructed from any number of transistors or other discrete circuit elements, which can individually or collectively assume any number of states. More specifically, the processing unit(s) 702 can operate as a finite-state machine, in response to executable instructions contained within the software modules disclosed herein.

These computer-executable instructions can transform the processing unit(s) 702 by specifying how the processing unit(s) 702 transitions between states, thereby transforming the transistors or other discrete hardware elements constituting the processing unit(s) 702.

Encoding the software modules presented herein can also transform the physical structure of the computer-readable media presented herein. The specific transformation of the physical structure depends on various factors, in different implementations of this description. Examples of such factors include, but are not limited to, the technology used to implement the computer-readable media, whether the computer-readable media is characterized as primary or secondary storage, and the like. For example, if the computer-readable media is implemented as semiconductor-based memory, the software disclosed herein can be encoded on the computer-readable media by transforming the physical state of the semiconductor memory. For instance, the software can transform the state of transistors, capacitors, or other discrete circuit elements constituting the semiconductor memory. The software can also transform the physical state of such components to store data thereupon.

As another example, the computer-readable media disclosed herein can be implemented using magnetic or optical technology. In such implementations, the software presented herein can transform the physical state of magnetic or optical media, when the software is encoded therein. These transformations can include altering the magnetic characteristics of particular locations within given magnetic media. These transformations can also include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer 700 to store and execute the software components presented herein. It also should be appreciated that the architecture shown in FIG. 7 for the computer 700, or a similar architecture, can be utilized to implement many types of computing devices such as desktop computers, notebook computers, servers, supercomputers, gaming devices, tablet computers, and other types of computing devices known to those skilled in the art. For example, the computer 700 may be wholly or partially integrated into the synthesizer 606. It is also contemplated that the computer 700 might not include all of the components shown in FIG. 7, can include other components that are not explicitly shown in FIG. 7, or can utilize an architecture completely different than that shown in FIG. 7.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method of enzymatic synthesis of a polynucleotide, the method comprising:
 a. contacting a first primer region of a universal template strand comprising universal base analogs with a complementary primer;
 b. removing a blocking group;
 c. contacting the universal template strand with a protected nucleotide selected according to a predetermined polynucleotide sequence and a polymerase so that the protected nucleotide is incorporated into the polynucleotide hybridized to the universal template strand; and
 d. repeating steps b-c to synthesize the polynucleotide.

Clause 2. The method of clause 1, wherein the universal template strand comprises a universal region consisting of a mixture of natural bases and the universal base analogs.

Clause 3. The method of clause 2, wherein the natural bases are present at regular intervals among the universal base analogs.

Clause 4. The method of any of clauses 1-3, wherein the universal base analogs comprise hydrogen bonding bases that form hydrogen bonds with any natural nucleobases.

Clause 5. The method of any of clauses 1-3, wherein the universal base analogs consist of inosine and derivative thereof.

Clause 6. The method of any of clauses 1-5, wherein the complementary primer includes the blocking group.

Clause 7. The method of any of clauses 1-6, wherein the blocking group is a 3' blocking group.

Clause 8. The method any of clauses 1-7, wherein the complementary primer has a $T_m$ that is greater than 60° C.

Clause 9. The method of any of clauses 1-8, wherein the blocking group is thermolabile, acid-labile, redox-labile, or photolabile.

Clause 10. The method of any of clauses 1-9, wherein the polymerase is a DNA-dependent DNA polymerase.

Clause 11. The method of any of clauses 1-10, wherein the polymerase is terminal deoxynucleotidyl transferase (TdT).

Clause 12. The method of any of clauses 1-11, wherein a backbone of the universal template strand comprises peptide nucleic acids, bridged nucleic acids, locked nucleic acids, or ribose phosphate with a 2'-deoxy substitution.

Clause 13. The method of any of clauses 1-12, further comprising: determining that synthesis of the predetermined polynucleotide sequence of the polynucleotide is complete; and dehybrizing the polynucleotide from the universal template strand.

Clause 14. The method of any of clauses 1-13, wherein the universal template strand further comprises a second primer region and the method further comprises contacting the universal template strand with a mixture of nucleotides without blocking groups.

Clause 15. A method of synthesizing a plurality of polynucleotides having different, predetermined sequences, the method comprising:
 a. contacting primer regions of a plurality of universal template strands comprising universal base analogs with complementary primers, wherein the universal template strands are bound to a solid substrate;
 b. removing blocking groups from nucleotides hybridized to a subset of the universal template strands;
 c. contacting the plurality of universal template strands with a protected nucleotide selected according to a predetermined polynucleotide sequence and a polymerase so that the protected nucleotide is incorporated into polynucleotides hybridized to the subset of the universal template strands; and d. repeating steps b-c with variations in the subset of the universal template strands and in a base of the protected nucleotide to synthesize the plurality of polynucleotides having different, predetermined sequences.

Clause 16. The method of clause 15, wherein the solid substrate comprises a microelectrode array and removing the blocking groups comprises activating a subset of electrodes in the microelectrode array.

Clause 17. The method of clause 16, wherein the blocking groups are removed by a redox reaction.

Clause 18. A system for synthesizing a plurality of polynucleotides having different, predetermined sequences, the system comprising: a solid substrate coated with a plurality of universal template strands comprising universal base analogs; a reaction chamber containing the solid substrate; a plurality of fluid delivery pathways each configured to introduce a single species of protected nucleotide into the reaction chamber; and control circuitry configured to selectively change local conditions on a portion of the surface of the solid substrate resulting in cleavage of blocking groups attached to the protected nucleotides and to selectively open the plurality of fluid delivery pathways to introduce protected nucleotides into the reaction chamber according to a predetermined polynucleotide sequence.

Clause 19. The system of clause 18, wherein the solid substrate comprises a microelectrode array and the control circuitry is configured to selectively activate electrodes in the microelectrode array.

Clause 20. The system of clause 18 or 19, wherein the universal template strands comprise primer regions and the system further comprises a fluid delivery pathway configured to introduce complementary primers each having a blocking group into the reaction chamber.

Conclusion

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

For ease of understanding, the processes discussed in this disclosure are delineated as separate operations represented as independent blocks. However, these separately delineated operations should not be construed as necessarily order dependent in their performance. The order in which the processes are described is not intended to be construed as a limitation, and unless other otherwise contradicted by context any number of the described process blocks may be combined in any order to implement the process or an alternate process. Moreover, it is also possible that one or more of the provided operations is modified or omitted.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications throughout this specification. Each of the cited references is individually incorporated herein by reference for its particular cited teachings as well as for all that it discloses.

The invention claimed is:

1. A method of enzymatic synthesis of a polynucleotide, the method comprising:
    a. contacting a first primer region of a universal template strand comprising universal base analogs with a complementary primer, wherein the universal template strand comprises a universal region consisting of a mixture of natural bases and the universal base analogs;
    b. removing a blocking group;
    c. contacting the universal template strand with a protected nucleotide selected according to a predetermined polynucleotide sequence and a polymerase so that the protected nucleotide is incorporated into the complementary primer or extended version thereof hybridized to the universal template strand; and
    d. repeating steps b-c to synthesize the polynucleotide.

2. The method of claim 1, wherein the natural bases are present at regular intervals among the universal base analogs.

3. The method of claim 1, wherein the universal base analogs comprise hydrogen bonding bases that form hydrogen bonds with any natural nucleobases.

4. The method of claim 1, wherein the universal base analogs consist of inosine and derivative thereof.

5. The method of claim 1, wherein the complementary primer includes the blocking group.

6. The method of claim 1, wherein the blocking group is a 3' blocking group.

7. The method of claim 1, wherein the complementary primer has a $T_m$ that is greater than 60° C.

8. The method of claim 1, wherein the blocking group is thermolabile, acid-labile, redox-labile, or photolabile.

9. The method of claim 1, wherein the polymerase is a DNA-dependent DNA polymerase.

10. The method of claim 1, wherein the polymerase is terminal deoxynucleotidyl transferase (TdT).

11. The method of claim 1, wherein a backbone of the universal template strand comprises peptide nucleic acids, bridged nucleic acids, locked nucleic acids, or ribose phosphate with a 2'-deoxy substitution.

12. The method of claim 1, further comprising:
    determining that synthesis of the predetermined polynucleotide sequence of the polynucleotide is complete; and dehybrizing the polynucleotide from the universal template strand.

13. The method of claim 1, wherein the universal template strand further comprises a second primer region and the method further comprises contacting the universal template strand with a mixture of nucleotides without blocking groups.

14. A method of synthesizing a plurality of polynucleotides having different, predetermined sequences, the method comprising:
   a. contacting primer regions of a plurality of universal template strands with complementary primers, wherein the universal template strands comprise universal regions consisting of a mixture of natural bases and universal base analogs and the universal template strands are bound to a solid substrate;
   b. removing blocking groups from nucleotides hybridized to a subset of the universal template strands;
   c. contacting the plurality of universal template strands with a protected nucleotide selected according to a predetermined polynucleotide sequence and a polymerase so that the protected nucleotide is incorporated into one or more complementary primers or extended versions thereof hybridized to the subset of the universal template strands; and
   d. repeating steps b-c with variations in the subset of the universal template strands and in a base of the protected nucleotide to synthesize the plurality of polynucleotides having different, predetermined sequences.

15. The method of claim 14, wherein the solid substrate comprises a microelectrode array and removing the blocking groups comprises activating a subset of electrodes in the microelectrode array.

16. The method of claim 15, wherein the blocking groups are removed by a redox reaction.

17. A system for synthesizing a plurality of polynucleotides having different, predetermined sequences, the system comprising:
   a solid substrate coated with a plurality of universal template strands comprising primer regions and universal regions, wherein the universal regions comprise a mixture of natural bases and universal base analogs;
   a reaction chamber containing the solid substrate;
   a plurality of fluid delivery pathways each configured to introduce a single species of protected nucleotide into the reaction chamber; and
   control circuitry configured to selectively change local conditions on a portion of the surface of the solid substrate resulting in cleavage of blocking groups attached to the protected nucleotides and to selectively open the plurality of fluid delivery pathways to introduce protected nucleotides into the reaction chamber according to a predetermined polynucleotide sequence.

18. The system of claim 17, wherein the solid substrate comprises a microelectrode array and the control circuitry is configured to selectively activate electrodes in the microelectrode array.

19. The system of claim 17, further comprises a fluid delivery pathway configured to introduce complementary primers each having a blocking group into the reaction chamber.

20. The system of claim 17, wherein the natural bases are present at regular intervals among the universal base analogs.

* * * * *